United States Patent [19]

Zinnen

[11] Patent Number: 4,797,233
[45] Date of Patent: Jan. 10, 1989

[54] PROCESS FOR SEPARATING MONO-, DI- AND TRIGLYCERIDES

[75] Inventor: Hermann A. Zinnen, Evanston, Ill.

[73] Assignee: UOP Inc., Des Plaines, Ill.

[21] Appl. No.: 898,300

[22] Filed: Aug. 20, 1986

[51] Int. Cl.[4] .............................................. C11C 1/08
[52] U.S. Cl. ................................................ 260/428.5
[58] Field of Search .............................. 260/428.5, 428

[56] References Cited

U.S. PATENT DOCUMENTS

| | | | |
|---|---|---|---|
| 2,639,289 | 5/1953 | Vogel | 260/428 |
| 2,771,480 | 11/1956 | Chasanov et al. | 260/420 |
| 2,985,589 | 5/1961 | Broughton et al. | 210/34 |
| 3,706,812 | 12/1972 | DeRosset et al. | 260/674 |
| 4,048,205 | 9/1977 | Neuzil et al. | 260/428 |
| 4,049,688 | 9/1977 | Neuzil et al. | 260/428 |
| 4,066,677 | 1/1978 | de Rosset et al. | 260/428 |
| 4,098,205 | 7/1978 | Kawashima et al. | 112/217 |
| 4,210,594 | 7/1980 | Logan et al. | 260/428 |
| 4,213,913 | 7/1980 | de Rosset | 260/428 |
| 4,402,832 | 9/1983 | Gerhold | 210/659 |

OTHER PUBLICATIONS

Grasas Y. Aceites 25 (5), pp. 280–284 (1974), by J. L. Lopez Ruiz et al. Abstract.
Continuous Adsorptive Processing–A New Separation Technique by D. B. Broughton presented at the 34th Annual Meeting of the Society of Chemical Engineers at Tokyo, Japan on Apr. 2, 1969.
The Separation of P-Xylene from $C_8$ Hydrocarbon Mixtures by the Parex Process, Broughton et al., presented at the Third Joint Annual Meeting, American Institute of Chemical Engineers, San Juan, Puerto Rico, May 17 through May 20, 1970.

Primary Examiner—J. E. Evans
Attorney, Agent, or Firm—Thomas K. McBride; John F. Spears, Jr.; Jack H. Hall

[57] ABSTRACT

The separation of monoglycerides from diglycerides and triglycerides is performed by an adsorptive chromatographic process in liquid phase using sodium, magnesium, lithium or potassium-exchanged X zeolites or potassium or sodium-exchanged Y zeolite, or potassium-exchanged L zeolite as the adsorbent. A ketone or ketone/n-aliphatic hydrocarbon can be selected as the desorbent.

10 Claims, 12 Drawing Sheets

PROCESS FOR SEPARATING MONO-, DI- AND TRIGLYCERIDES

FIELD OF THE INVENTION

The field of art to which this invention belongs is the solid bed adsorptive separation of glycerides. More specifically, the invention relates to a process for separating monoglycerides from di- and triglycerides by a process which employs Na, Mg, Li, or K-exchanged X, or Na or K-exchanged Y, or potassium-exchanged L zeolites.

BACKGROUND OF THE INVENTION

The separation of many classes of compounds by selective adsorption on molecular sieves or zeolites as well as other adsorbents is well known. For example, as disclosed in U.S. Pat. No. 4,048,205, methyl esters of fatty acids of various degrees of unsaturation may be separated from mixtures of esters of saturated and unsaturated fatty acids with X or Y zeolites exchanged with a selected cation. Further in U.S. Pat. No. 4,353,838 it is disclosed that monoethanoid fatty acids may be separated from diethanoid fatty acids with crosslinked polystyrenes, e.g. "Amberlite". The refining of oils by admixing them with magnesium silicate to adsorb coloring matter and free fatty acids from glyceride oils is disclosed in U.S. Pat. No. 2,639,289. Subsequently, it has been suggested in U.S. Pat. No. 2,771,480 to use ion-exchange resins to adsorb the impurities found in glyceride oils. In an article by J. L. Lopez Ruiz et al., Grasas Y. Aceites 25 (5) pp. 280–84 (1974) the separation of monooleins from trioleins by adsorption on a Linde X zeolite (calcium-exchanged X type) was disclosed with desorption by ethyl alcohol. This has the disadvantage that ethyl alcohol can cause transesterification of the triglycerides to form mono- and diglycerides and fatty acid ethyl esters.

The process of separating monoglycerides from di- and triglycerides described herein has many potential uses, for example, the purification of triglycerides, e.g. palm oil, by crystallization, is affected by the presence of monoglycerides. A process which separates monoglycerides from triglycerides can improve the purity and recovery of such crystallizations. Another application of our separation process results from the use of mono- and diglycerides as emulsifiers in large amounts in the food industry. These compounds are produced in ways, i.e., the reaction of glycerol with a fatty acid such as stearic acid, or with triglyceride mixtures such as tallow, which results in a mixture of 1- and 2-monoglycerides, 1,2-diglycerides and 1,3-diglycerides. Separation of the components of the mixture is currently accomplished by molecular distillation, a process requiring high temperatures and high vacuum and which, nevertheless, results in low purities and yields. Applicant's discovery provides real benefits in terms of energy savings and product purity and recovery.

Another important application of our separation process resides in the utility of the separated products, that is, pure monoglycerides and diglycerides, in the synthesis of triglycerides. Cocoa butter, for example, is a high value natural product consisting predominantly of a mixture of particular triglycerides where the 2-position of glycerol is esterified with an oleyl group and the 1- and 3-positions are esterified with either the palmitoyl or the stearyl group. When the 1- and 3-positions are esterified with palmitoyl groups, the triglyceride is referred to as "POP". Likewise, when a stearyl group occupies both 1- and 3-positions, the compound is called "SOS", and when 1- and 3-positions are filled by one palmitoyl and one stearyl group, the compound is referred to as "SOP". Cocoa butter is a predominant component in chocolate confections. It is believed that large quantities of these particular triglycerides could be synthesized and used as cocoa butter extenders. However, it is essential that the oleic acid moiety occurs at the 2-position. This can be assured by using the 2-oleyl-monoglyceride as precursor for such syntheses. A mixture of 2-monoglycerides and diglycerides can be obtained from the enzyme lipase, which is stereospecific and forms diglycerides and 2-monoglyceride from triglycerides. By reacting lipase with triglycerides containing the 2-oleyl group and separating the resulting mono- and diglycerides a 2-oleyl-monoglyceride could be produced. This separation can be achieved by the invention, whereby the extract will contain the desired 2-monoglyceride. Alternatively, it is possible to synthesize the aforementioned triglycerides by using as precursors 1,3-diglycerides containing palmitoyl and stearyl groups and adding the oleyl group in the 2 position, thereby affording triglycerides such as POP, SOP, and SOS. The process of the instant invention can be used to accomplish this by separation of glyceride mixtures which contain 1,3-diglycerides, obtaining the desired 1,3-diglycerides in the raffinate.

I have discovered combinations of zeolites and desorbents which separate the monoglycerides and diglycerides. The monoglycerides are adsorbed to the substantial exclusion of diglycerides and are concentrated in the extract. The diglycerides, therefore, are removed from the mixture of monoglycerides and diglycerides and are concentrated in the raffinate of the adsorptive separation apparatus.

SUMMARY OF THIS INVENTION

The present invention is a process for separating monoglycerides from a feed mixture comprising monoglycerides and at least one diglyceride and may additionally contain at least one triglyceride. The process comprises contacting the mixture at adsorption conditions with an adsorbent comprising an X type zeolite exchanged with potasssium, magnesium, lithium or sodium ion, or a Y type zeolite exchanged with potassium or sodium, or an L type zeolite exchanged with potassium. The monoglyceride is selectively adsorbed to the substantial exclusion of the diglycerides and triglycerides. Next, the monoglyceride is desorbed by a liquid ketone or a mixture of a ketone and paraffin desorbents. Diglycerides and triglycerides, if present, are removed before the monoglycerides and, together with part of the desorbent, constitute the raffinate. The desorbent may be selected from the ketones having up to 7 carbons, e.g., acetone, the pentanones, hexanones and heptanones. Specific examples of desorbent liquids useful in the process are acetone, methylethyl ketone, diethyl ketone, methylpropyl ketone, 2-hexanone, 2-heptanone, etc. and mixtures thereof with hexane.

The steps of the process are: (a) maintaining net fluid flow through a column of the adsorbent in a single direction, which column contains at least three zones having separate operational functions occurring therein and being serially interconnected with the terminal zones of the column connected to provide a continuous connection of the zones; (b) maintaining an adsorption zone in the column, the zone defined by the adsorbent located between a feed input stream at an upstream boundary of the zone and a raffinate output stream at a downstream boundary of the zone; (c) maintaining a purification zone immediately upstream from the adsorption zone, the purification zone defined by the adsorbent located between an extract output stream at an upstream boundary of the purification zone and the feed input stream at a downstream boundary of the purification zone; (d) maintaining a desorption zone immediately upstream from the purification zone, the desorption zone defined by the adsorbent located between a desorbent input stream at an upstream boundary of the zone and the extract output stream at a downstream boundary of the zone; (e) passing the feed mixture into the adsorption zone at adsorption conditions to effect the selective adsorption of the monoglycerides by the adsorbent in the adsorption zone and withdrawing a raffinate output stream from the adsorption zone; (f) passing a desorbent material into the desorption zone at desorption conditions to effect the displacement of the monoglycerides from the adsorbent in the desorption zone; (g) withdrawing an extract output stream comprising monoglycerides and desorbent material from the desorption zone; (h) withdrawing a raffinate output stream comprising diglycerides from the desorption zone; (i) periodically advancing through the column of adsorbent in a downstream direction with respect to fluid flow in the adsorption zone, the feed input stream, raffinate output stream, desorbent input stream, and extract output stream to effect the shifting of zones through the adsorbent and the production of extract output and raffinate output streams.

Other embodiments of our invention encompass details about feed mixtures, adsorbents, desorbent materials and operating conditions all of which are hereinafter disclosed in the following discussion of each of the facets of the present invention.

DESCRIPTION OF THE INVENTION

The following definitions of various terms used throughout this specification will be used in describing the operation, objects and advantages of the present invention.

A "feed mixture" is a mixture containing one or more extract components and one or more raffinate components to be fed to an adsorbent of the process. The term "feed stream" indicates a stream of feed mixture which passes to an adsorbent used in the process.

An "extract component" is a type of compound or a compound that is more selectively adsorbed by the adsorbent while a "raffinate component" is a compound or type of compound that is less selectively adsorbed. In this process, monoglycerides are extract components and the diglycerides are raffinate components. The term "raffinate stream" or "raffinate output stream" means a stream through which a raffinate component is removed from an adsorbent. The composition of the raffinate stream can vary from essentially 100% desorbent material (hereinafter defined) to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated that an extract component is never completely adsorbed by the adsorbent, nor is a raffinate component completely nonadsorbed by the adsorbent. Therefore, small amounts of a raffinate component can appear in the extract stream, and likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, in one embodiment, the ratio of the concentration of the more selectively adsorbed monoglyceride to the concentration of less selectively adsorbed diglycerides will be highest in the extract stream, next highest in the feed mixture, and lowest in the raffinate stream. Likewise, the ratio of the less selectively adsorbed diglycerides to the more selectively adsorbed monoglycerides will be highest in the raffinate stream, next highest in the feed mixture, and the lowest in the extract stream. The term "desorbent material" shall mean generally a material capable of desorbing an extract component. The term "desorbent stream" or "desorbent input stream" indicates the stream through which desorbent material passes to the adsorbent. When the extract stream and the raffinate stream contain desorbent materials, at least a portion of the extract stream and preferably at least a portion of the raffinate stream from the adsorbent will be passed to separation means, typically fractionators, where at least a portion of the desorbent material will be separated at separation conditions to produce an extract product and a raffinate product. The terms "extract product" and "raffinate product" mean products produced by the process containing, respectively, an extract component and a raffinate component in higher concentrations than those found in the respective extract stream and the raffinate stream. The term "selective pore volume" of the adsorbent is defined as the volume of the adsorbent which selectively adsorbs extract components from a feed mixture. The term "nonselective void volume" of an adsorbent is the volume of an adsorbent which does not selectively retain an extract component from a feed mixture. This volume includes the cavities of the adsorbent which contain no adsorptive sites and the interstitial void spaces between adsorbent particles. The selective pore volume and the nonselective void volume are generally expressed in volumetric quantities and are of importance in determining the proper flow rates of fluid required to be passed into the process for efficient operations to take place for a given quantity of adsorbent.

The term "desorbent material" as used herein shall mean any fluid substance capable of removing a selectively adsorbed feed component from the adsorbent. Generally, in a swing-bed system in which the selectively adsorbed feed component is removed from the adsorbent by a purge stream, desorbent material selection is not too critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which employ zeolitic adsorbents and which are generally operated continuously at substantially constant pressures and temperatures to ensure liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract from displacing the desorbent material in a following adsorption cycle. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, the desorbent must not react with either the adsorbent or any component of the feed material and must not reduce or destroy the critical selectivity of the adsorbent for the extract components with respect to the raffinate component. Desorbent materials to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high. It is, therefore, contemplated that any desorbent material used in this process will have a substantially different average boiling point than that of the feed mixture to allow separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture.

In the preferred isothermal, isobaric, liquid-phase operation of the process of this invention, ketones, e.g., methylethyl ketone, diethyl ketone, acetone and mixtures of a ketone and a paraffinic hydrocarbon, e.g. hexane, have been found to be effective desorbents. The desorbent may be dissolved in a suitable diluent, such as hexane, so as to modify the rate of desorption as desired.

The prior art has recognized that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of an extract component with respect to a raffinate component and the desorbent material; and sufficiently fast rates of adsorption and desorption of the extract components to and from the adsorbent.

Capacity of the adsorbent for adsorbing a specific volume of one or more extract components is, of course, a necessity; without such capacity. the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (B) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases, respectively. The equilibrium conditions are determined when the feed passing over a bed of adsorbent does not change composition after contacting the bed of adsorbent. In other words, there is no net transfer of material occurring between the unadsorbed and adsorbed phases.

Where selectivity of two components approaches 1.0 there is no preferential adsorption of one component by the adsorbent with respect to the other; they are both adsorbed (or nonadsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally, desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material with the desorbent material or, in other words, the relative rate of desorption of the extract component. This characteristic relates directly to the amount of desorbent material that must be employed in the process to recover the extract component from the adsorbent;

faster rates of exchange reduce the amount of desorbent material needed to remove the extract component and, therefore, permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate, a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a nonadsorbed tracer (n-tetradecane for instance) and of the particular feed material all diluted in desorbent is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternately, effluent samples can be collected periodically and later analyzed separately by gas or liquid chromatography.

From information derived from the chromatographic traces, adsorbent performance can be rated in terms of capacity index for an extract component, selectivity for one isomer with respect to the other, and the rate of desorption of an extract component by the desorbent. The capacity index may be characterized by the distance between the center of the peak envelope of the selectively adsorbed isomer and the peak envelope of the tracer component or some other known reference point. It is expressed in terms of the volume in cubic centimeters of desorbent pumped during this time interval. Selectivity, (B), for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

The adsorbent to be used in the process of this invention comprises specific crystalline aluminosilicates. Crystalline aluminosilicates such as that encompassed by the present invention include crystalline aluminosilicate cage structures in which the alumina and silica tetrahedra are intimately connected in an open three-dimensional network. The tetrahedra are crosslinked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves," although widely used, is not strictly suitable since the separation of specific glycerides is apparently dependent on differences in electrochemical attraction of the different isomers and the adsorbent rather than solely on physical size differences in the isomer molecules.

In hydrated form, the crystalline aluminosilicates generally encompass those zeolites represented by the Formula below:

$$M_{2/n}O:Al_2O_3:wSiO_2:yH_2O \qquad \text{Formula 2}$$

where "M" is a cation which balances the electrovalence of the tetrahedra and is generally referred to as an exchangeable cationic site, "n" represents the valence of the cation, "w" represents the moles of $SiO_2$, and "y" represents the moles of water. The generalized cation "M" may be monovalent, divalent or trivalent cations or mixtures thereof.

The prior art has generally recognized that adsorbents comprising the type X and the type Y zeolites can be used in certain adsorptive separation processes. These zeolites are well known to the art.

The type X structured zeolite in the hydrated or partially hydrated form can be represented in terms of mole oxides as shown in Formula 3 below:

$$(0.9\pm0.2)M_{2/n}O:Al_2O_3:(2.5\pm0.5)SiO_2:yH_2O \qquad \text{Formula 3}$$

where "M" represents at least one cation having a valence of not more than 3, "n" represents the valence of "M", and "y" is a value up to about 9 depending upon the identity of "M" and the degree of hydration of the crystal. As noted from Formula 3, the Si mole ratio is 2.5 0.5. The cation "M" may be one or more of a number of cations such as the hydrogen cation, the alkali metal cation, or the alkaline earth cations, or other selected cations, and is generally referred to as an exchangeable cationic site. As the type X zeolite is initially prepared, the cation "M" is usually predominately sodium and the zeolite is, therefore, referred to as a sodium-type X zeolite. Depending upon the purity of the reactants used to make the zeolite, other cations mentioned above may be present, however, as impurities.

The type Y structured zeolite in the hydrated or partially hydrated form can be similarly represented in terms of mole oxides as in Formula 4 below:

$$(0.9\pm0.2)M_{2/n}O:Al_2O_3:wSiO_2:yH_2O \qquad \text{Formula 4}$$

where "M" is at least one cation having a valence not more than 3, "n" represents the valence of "M", "w" is a value greater than about 3 up to 6, and "y" is a value up to about 9 depending upon the identity of "M", and the degree of hydration of the crystal. The $SiO_2/Al_2O_3$ mole ratio for type Y structured zeolites can thus be from about 3 to about 6. Like the type X structured zeolite, the cation "M" may be one or more of a variety of cations but, as the type Y zeolite is initially prepared, the cation "M" is also usually predominately sodium.

The L zeolite in the hydrated or partially hydrated form may be represented in terms of mole oxides as in Formula 5 below:

$$0.9\text{--}1.3M_{2/n}O{:}Al_2O_3{:}5.2\text{--}6.9SiO_2{:}yH_2O \qquad \text{Formula 5}$$

where M designates at least one exchangeable cation as referred to above, n is the valence of M and y may be any value from 0 to about 9. It is preferred to synthesize the potassium form of the L type zeolite since the reactants to make this form are readily available and generally water soluble. Thus, the as-made form of the L zeolite is referred to as potassium-L, or K-L, zeolite. L-zeolite is characterized by planar 12-ring pores aligned to produce one-dimensional channels, linked to each other by small pore openings which will not admit water molecules. A minor two-dimensional pore system also exists, parallel to the aforesaid channels.

The present invention is based on the discovery that the type Y zeolite with potassium or sodium cations at exchangeable cation sites is more selective for the monoglycerides than for the diglycerides, and that the type X zeolite having potassium, lithium, magnesium or sodium cations at exchangeable cationic sites and that the type L zeolite having potassium cations at the exchangeable sites is likewise more selective for the monoglycerides than the diglycerides.

Typically, adsorbents used in separative processes contain the crystalline material dispersed in an amorphous binder material or inorganic matrix, having channels and cavities therein which enable liquid access to the crystalline material. Silica, alumina, or mixtures thereof are typical of such inorganic matrix materials. The binder aids in forming or agglomerating the crystalline particles which otherwise would comprise a fine powder. The adsorbent may thus be in the form of particles such as extrudates, aggregates, tablets, macrospheres or granules having a desired particle range, preferably from about 16 to about 60 mesh (Standard U.S. Mesh). Lower water content in the adsorbent is advantageous from the standpoint of having less water contamination of the product.

The adsorbent may be employed in the form of a dense fixed bed which is alternately contacted with a feed mixture and a desorbent material in which case the process will be only semicontinuous. In another embodiment, a set of two or more static beds of adsorbent may be employed with appropriate valving so that a feed mixture can be passed through one or more adsorbent beds of a set while a desorbent material is passed through one or more of the other beds in a set. The flow of a feed mixture and a desorbent material may be either up or down through an adsorbent in such beds. Any of the conventional apparatus employed in a static bed fluid-solid contacting may be used.

Moving bed or simulated moving bed flow systems, however, have a much greater separation efficiency than fixed bed systems and are, therefore, preferred. In the moving bed or simulated moving bed processes, the retention and displacement operations are continuously making place which allows both continuous production of an extract and a raffinate stream and the continual use of feed and displacement fluid streams. One preferred embodiment of this process utilizes what is known in the art as the simulated moving bed countercurrent flow system. In such a system, it is the progressive movement of multiple liquid access points down a molecular sieve chamber that simulates the upward movement of molecular sieve contained in the chamber. Reference can also be made to D. B. Broughton's U.S. Pat. No. No. 2,985,589, in which the operating principles and sequence of such a flow system are described, and to a paper entitled, "Continuous Adsorptive Processing—A New Separation Technique," by D. B. Broughton presented at the 34th Annual Meeting of the Society of Chemical Engineers at Tokyo, Japan on Apr. 2, 1969, both references incorporated herein by reference for further explanation of the simulated moving bed countercurrent process flow scheme.

Another eabodiment of a simulated moving bed flow system suitable for use in the process of the present invention is the cocurrent high efficiency simulated moving bed process disclosed in U.S. Pat. No. 4,402,832 to Gerhold, incorporated by reference herein in its entirety.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically, the concentration of desorbent material in the extract product and the raffinate product will be less than about 5 vol. % and more preferably less than about 1 vol. %. The separation means will typically be a fractionation column, the design and operation of which is well known to the separation art.

Although both liquid and vapor phase operations can be used in many adsorptive separation processes, liquid-phase operation is preferred for this process because of the lower temperature requirements and because of the higher yields of an extract product that can be obtained with liquid-phase operation over those obtained with vapor-phase operation. Adsorption conditions will include a temperature range of from about 20° C. to about 250° C. with about 100° C. to about 200° C. being more preferred and a pressure sufficient to maintain liquid phase. Desorption conditions will include the same range of temperatures and pressure as used for adsorption conditions.

The size of the units which can utilize the process of this invention can vary anywhere from those of pilot-plant scale (see for example U.S. Pat. No. 3,706,812) to those of commercial scale and can range in flow rates from as little as a few cc's an hour up to many thousands of gallons per hour.

The following examples are presented for illustration purposes and more specifically are presented to illustrate the selectivity relationships that make the process of the invention possible. Reference to specific cations, desorbent materials, feed mixtures and operating condi-

EXAMPLE I

In this experiment, the pulse test was performed to evaluate the ability of the present invention to separate monoglycerides from diglycerides. The adsorbent used was a potassium-exchanged X zeolite and can be prepared by mixing with 15 wt. % clay. Water is then added and the resulting mixture is extruded, calcined at about 400° C., then ground to 20-50 mesh size. The adsorbent was redried at 350° C. before it was utilized in the process in each test. It was noted that some adsorbents caused reactivity when exposed to the glyceride mixture, in particular transesterification reactions due to basicity of the adsorbent. It was found that this reactivity could be eliminated by deactivating the adsorbent with treatments which consumed this basicity, such as washing the adsorbent with aqueous solutions of sugars. Alternatively, material such as acid solutions or buffers could be used for adsorbent deactivation. For example, a commercially obtained potassium X faujasite was dried at 350° C. and tested for reactivity in the above-described pulse test apparatus without treatment for deactivation. The desorbent used was methylethyl ketone (MEK) and the temperature was 70° C. The feed for this experiment was 2.6 cc of a solution containing 0.5 g pure glycerol monostearate and 2 cc MEK.

Figure 1A:
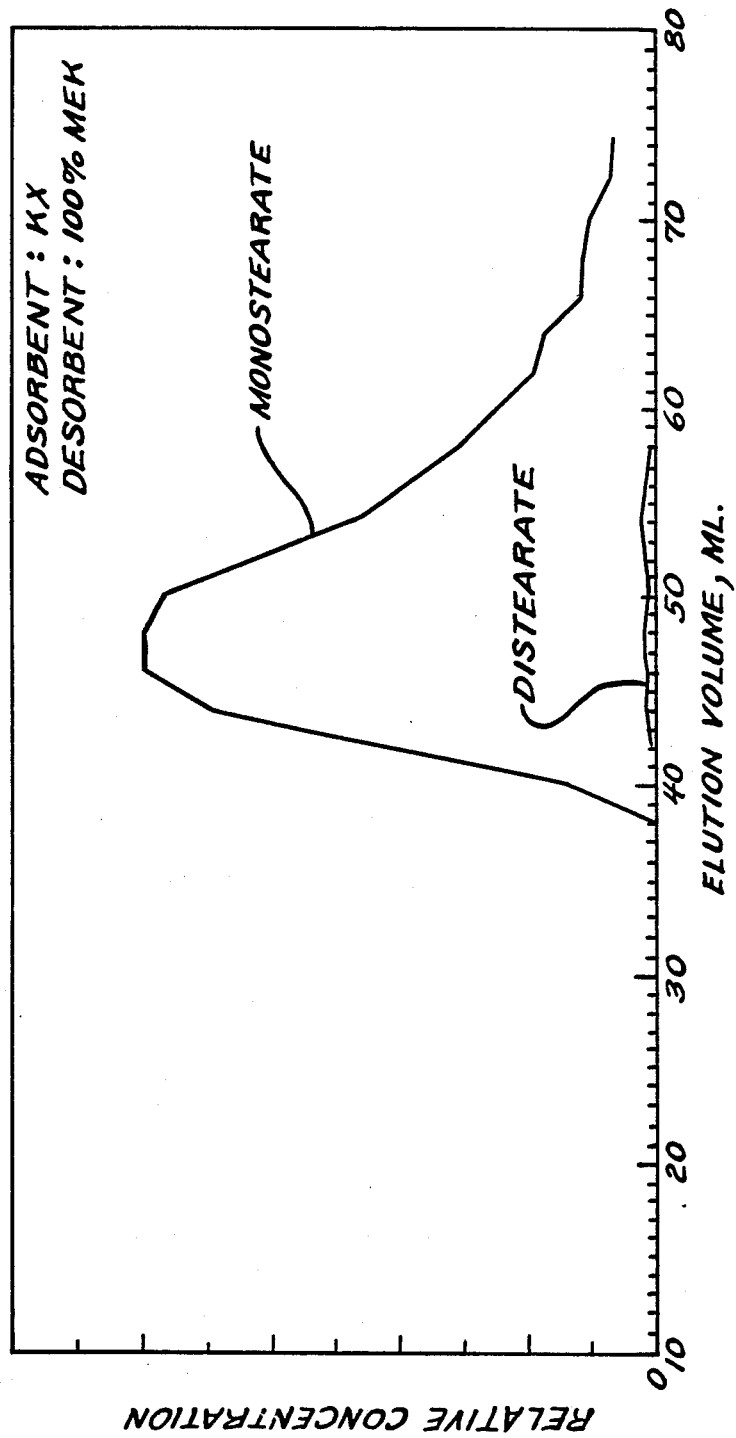
FIGS. 1-10 are chromatographic traces of the pulse tests described in Examples I through XI, illustrating the separations achieved with various zeolites and desorbents.

The testing apparatus was the above-described pulse test apparatus. The results of the test are illustrated in FIG. 1a, which shows that in addition to glycerol monostearate, glycerol distearate was present in the column effluent, indicating transesterification was taking place in the column.

Figure 1B:
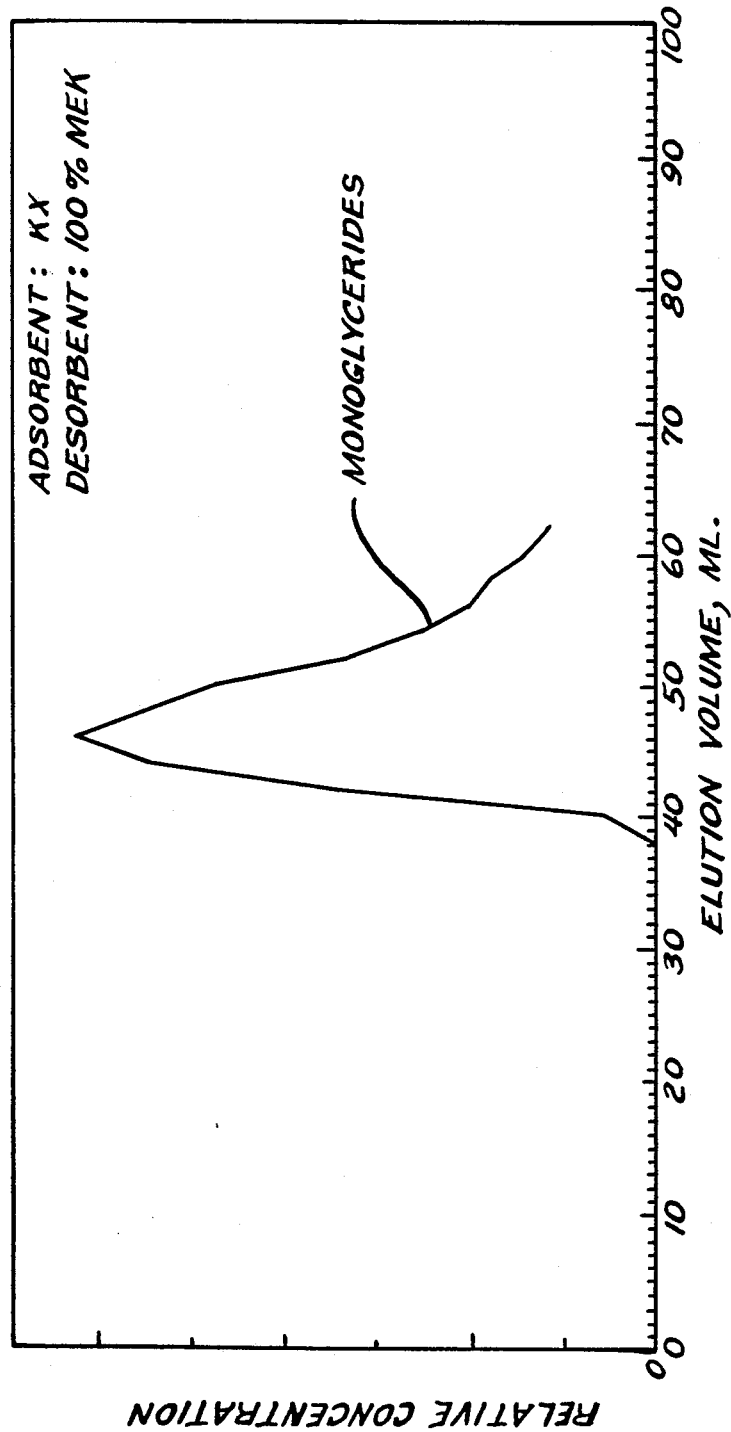

A similar experiment was conducted, except that the adsorbent was deactivated by the following procedure: a 1200 cc column packed with the adsorbent was washed with an aqueous glucose solution containing 40% dissolved solids at a rate of about 140 cc hour until the base catalyzed conversion of glucose to fructose was nil. The adsorbent was then washed with water to remove any sugars, dried, and tested as in the above case. In this case analysis of the column effluent showed no production of glycerol distearate, FIG. 1b.

The deactivated adsorbent so produced was used to evaluate the ability of the present invention to separate monoglycerides from diglycerides. For this pulse test, the column was maintained at a temperature of 65° C. and a pressure of 50 psig. Liquid chromatographic analysis equipment was used to analyze the column effluent stream in order to determine the composition of the effluent material at given time intervals. The feed mixture employed for each test comprised 2 cc pulses of a mixture containing 1.0 g of a glyceride mixture, 0.3 g n-tetradecane, which was used as a tracer, and 1.5 ml of methylethyl ketone (MEK). The glyceride mixture had approximately the following composition:

| | |
|---|---|
| monoglycerides: | 45.1% |
| | monopalmitate: 5.1% |
| | monostearate: 40% |
| diglycerides: | 51.5% |
| | dipalmitin: 1.9% |
| | 1-palmitoyl-3-stearyl-glycerol: 8.4% |
| | 2-palmitoyl-3-stearyl-glycerol: 5% |
| | 1,3-distearyl glycerol: 24% |
| | 1,2-distearyl glycerol: 12.2% |
| triglycerides: | 2% |
| stearic acid: | 1.4% |

The operations taking place for each test were as follows. The desorbent material was run continuously at a nominal liquid hourly space velocity (LHSV) of 1.0. At some convenient time interval, a pulse of the feed mixture was introduced. The desorbent stream was then resumed at 1 LHSV and continued to pass into the adsorbent column until all of the feed components had been eluted from the column as determined by chromatographic analysis of the effluent material leaving the adsorption column. In most cases, the column effluent is analyzed for its mono- and diglyceride content; however, it was determined by complete analysis (Example X) that the triglycerides in the feed mixture are relatively unadsorbed and thus elute and are separated with the diglycerides, while the stearic acid in the feed mixture elutes with the monoglycerides.

Figure 1C:
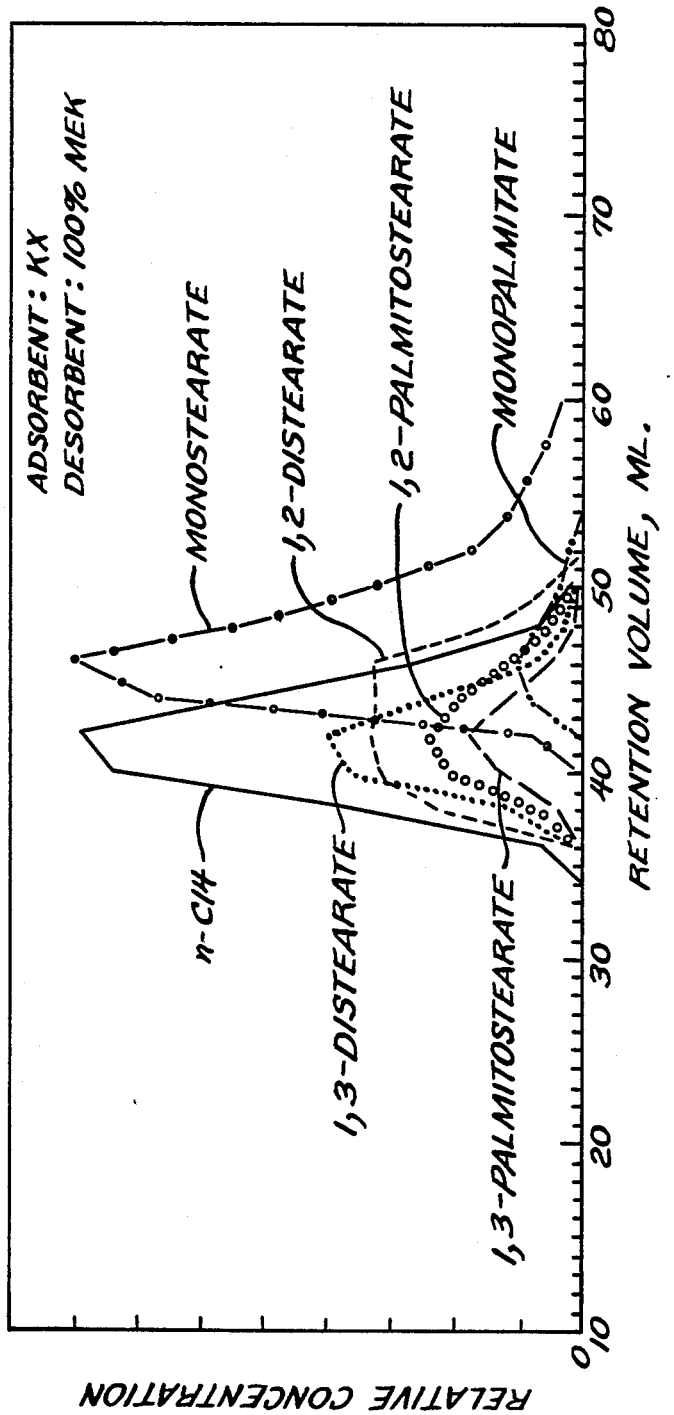

The results of the test of this Example are shown on the accompanying FIG. 1c which comprises the chromatographic trace.

It is clear from the test that the separation of monoglycerides from diglycerides is readily achieved by the process of the present invention. There is sufficient resolution between the monoglyceride curve and curves for the diglycerides for the separation. From equation 1, selectivities for the monoglycerides relative to the diglycerides approach infinity because the diglycerides have no significant retention volume. Note that all the different diglycerides of the mixture display such nonadsorptive behavior and are separated as a group, forming a raffinate product; likewise, all the monoglycerides of the mixture display similar adsorptive behavior and are extracted as a group, forming an extract product. Thus, analysis of the effluent for one monoglyceride, for example monostearate, and one diglyceride, for example distearate, serves to define the total monoglyceride and diglyceride elution from the adsorbent column. The monoglyceride retention volume was 4.5 cc.

EXAMPLE II

The pulse test of Example I was repeated for Y type molecular sieves. In this test, a type Y potassium-exchanged zeolite was used. he temperature was 120° C. and the desorbent was 25 vol. % acetone in hexane.

Figure 2:
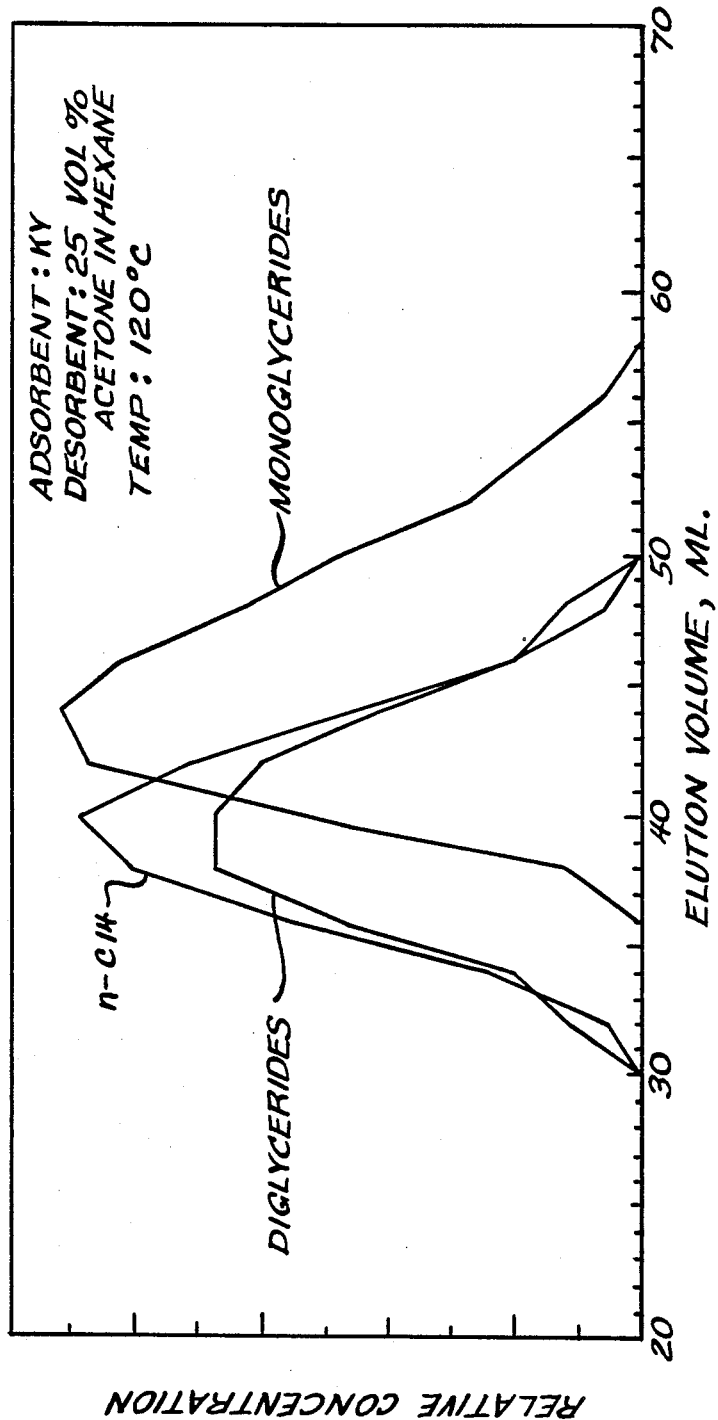

It is clear from FIG. 2, which yields a monoglyceride retention volume of 5.2 cc, that the adsorbent of the present invention exhibits acceptable selectivity for the monoglycerides.

EXAMPLE III

The pulse test of Example II was repeated except that 100% acetone was used for the desorbent. The feed composition was as follows:

| | |
|---|---|
| 0.3 g monoolein | 99% 1-monooleyl glyceride |
| | 1% 2-monooleyl glyceride |
| 0.3 g diolein | 15% 1,2-dioleyl glyceride |
| | 85% 1,3-dioleyl glyceride |

-continued 0.2 g n-C$_{14}$
2.1 cc diethyl ketone (DEK)

Figure 3:
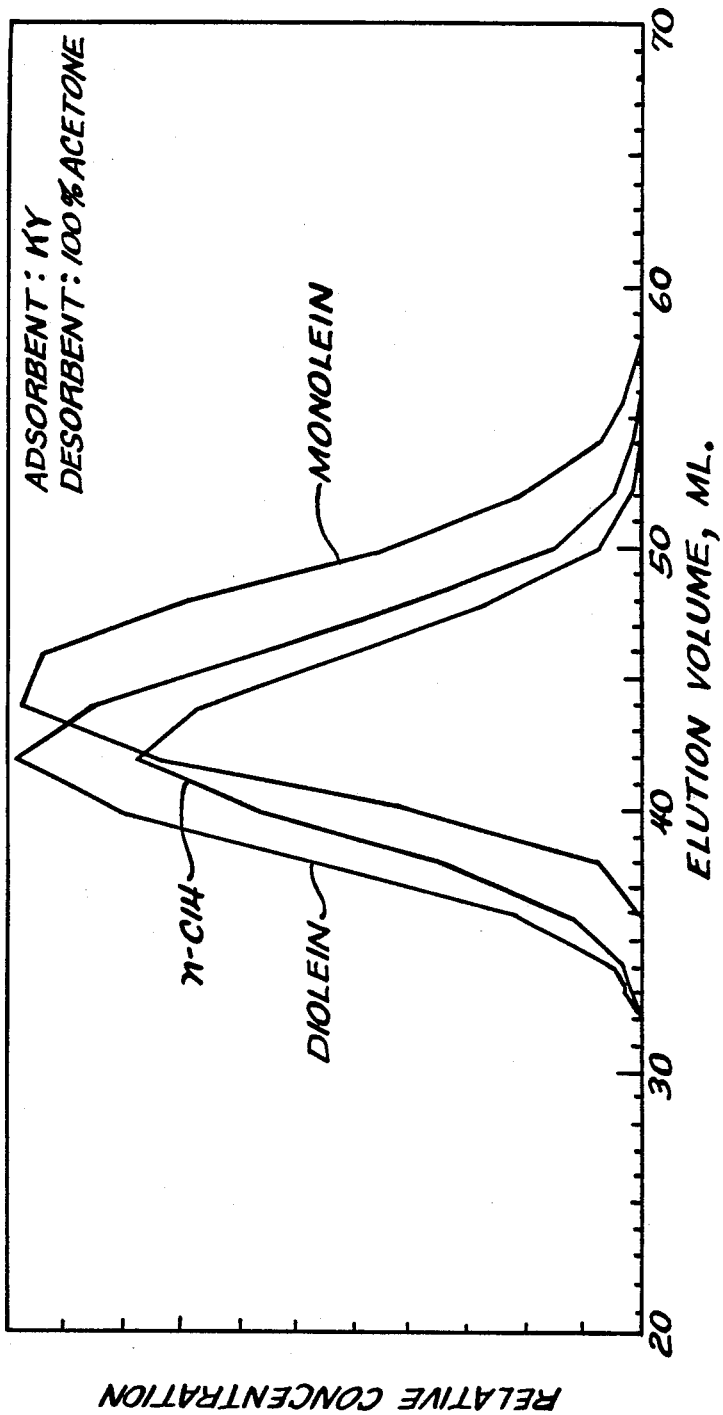

The retention volume of the monooleins was 2.7 cc, as seen in FIG. 3.

EXAMPLE IV

Figure 4:
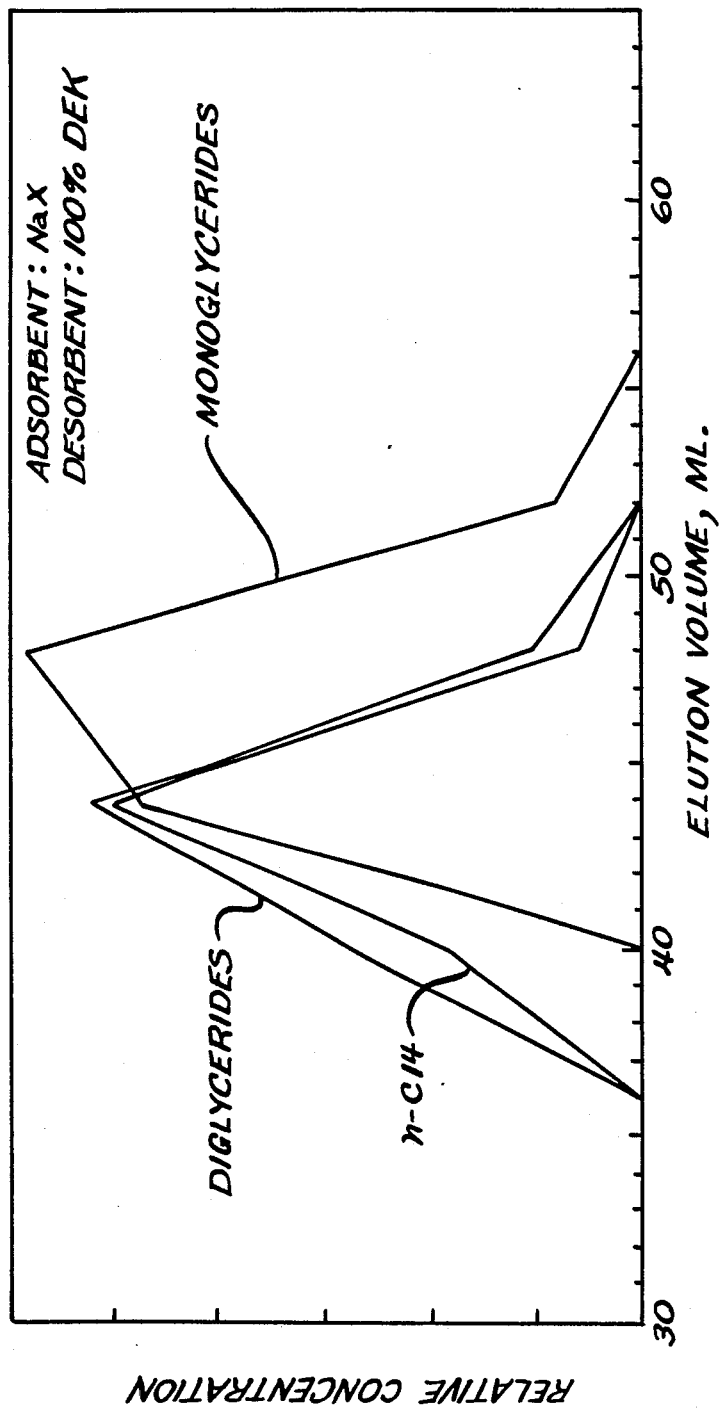

The pulse test of Example I was repeated except that diethyl ketone was used for desorbent, Na-X was the adsorbent, and the temperature was 120° C. A monoglyceride retention volume of 2.5 cc was obtained, as seen in FIG. 4.

EXAMPLE V

Figure 5:
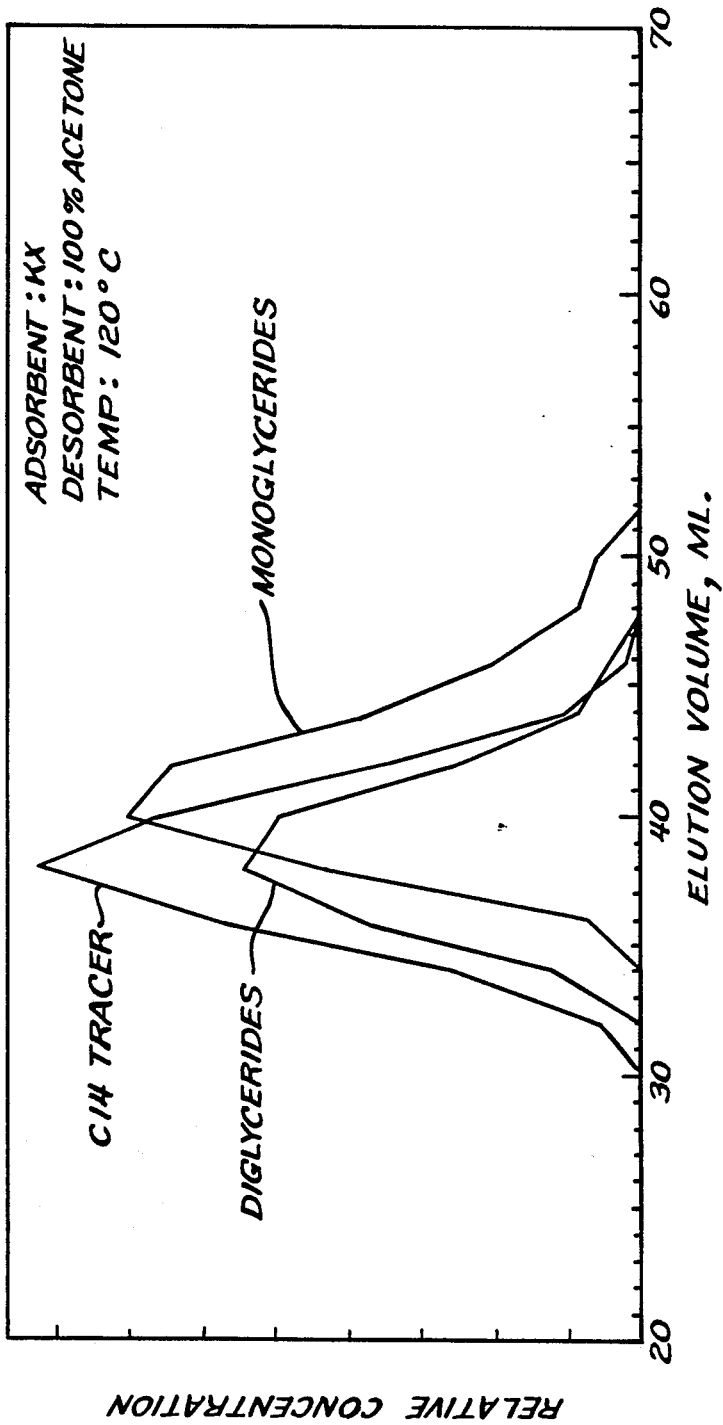

The pulse test of Example I was repeated with the same feed, but with 100% acetone as desorbent and X type zeolite exchanged with potassium ions. The temperature of the test was 120° C. A monoglyceride retention volume of 2.5 cc was obtained from the liquid chromatographic plot shown in FIG. 5.

EXAMPLE VI

Figure 6:
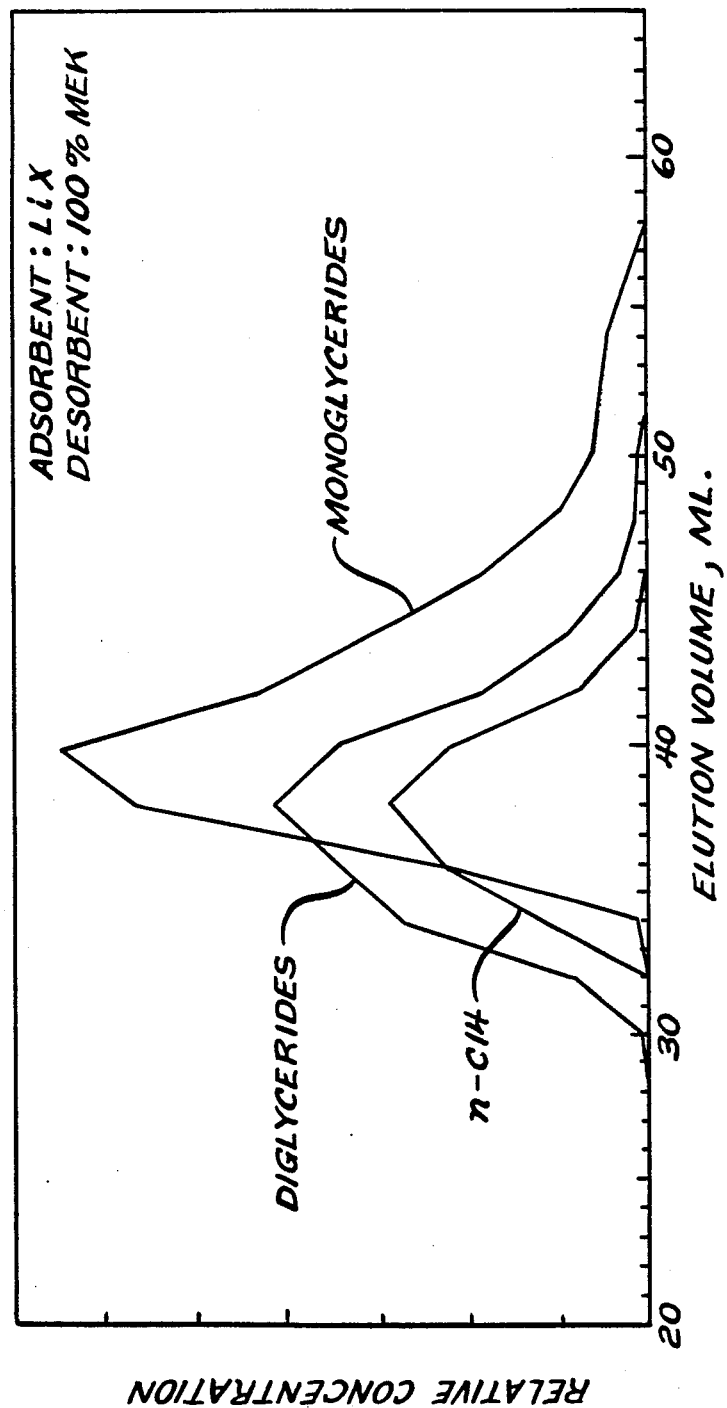

The pulse test of Example I was repeated except that adsorbent was an X type zeolite exchanged with lithium and the temperature was 70° C. It is clear from FIG. 6, which yields a monoglyceride retention volume of 2.9 cc, that LiX adsorbent exhibits acceptable selectivity for monoglycerides.

EXAMPLE VII

Figure 7:
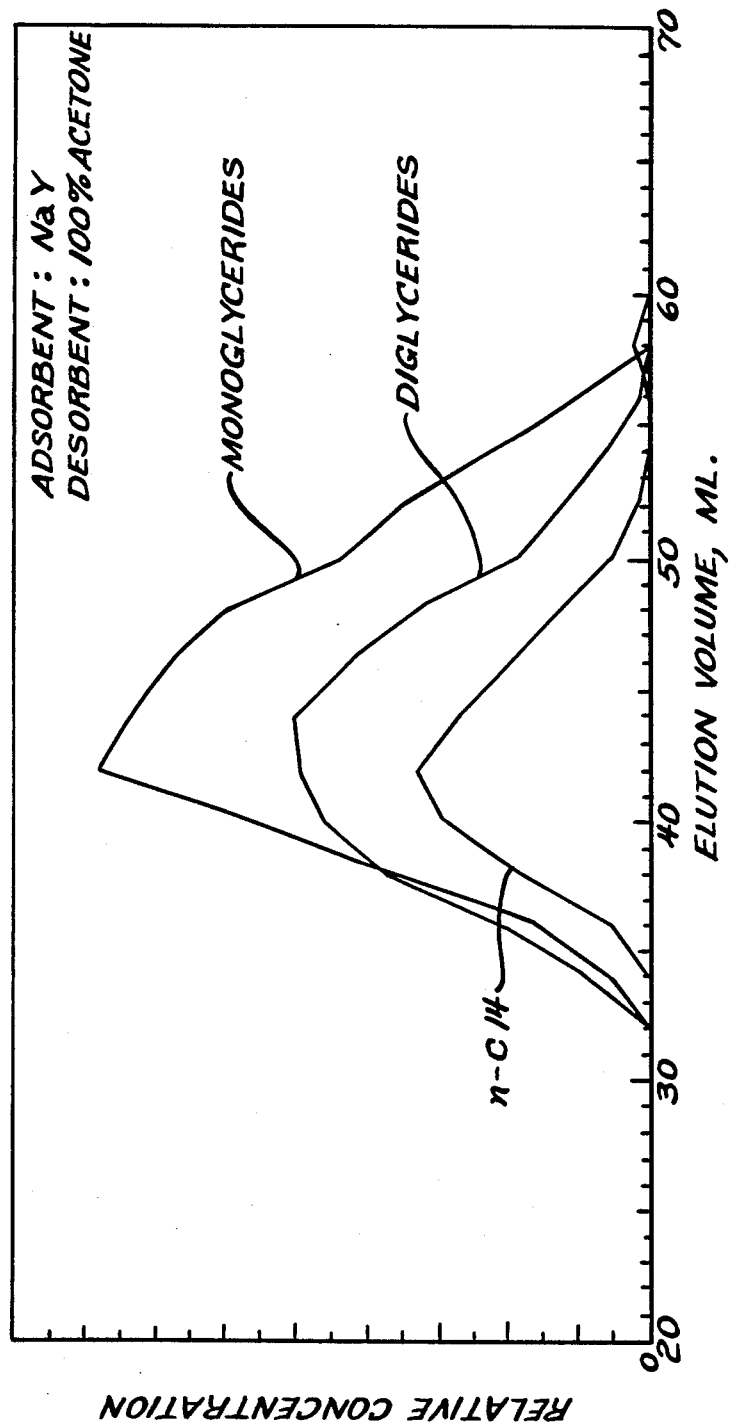

The pulse test of Example III was repeated except that the Y type zeolite adsorbent was exchanged with sodium. Analysis of the test, shown in FIG. 7, gives a monoglyceride retention volume of 2.1 cc.

EXAMPLE VIII

Figure 8:
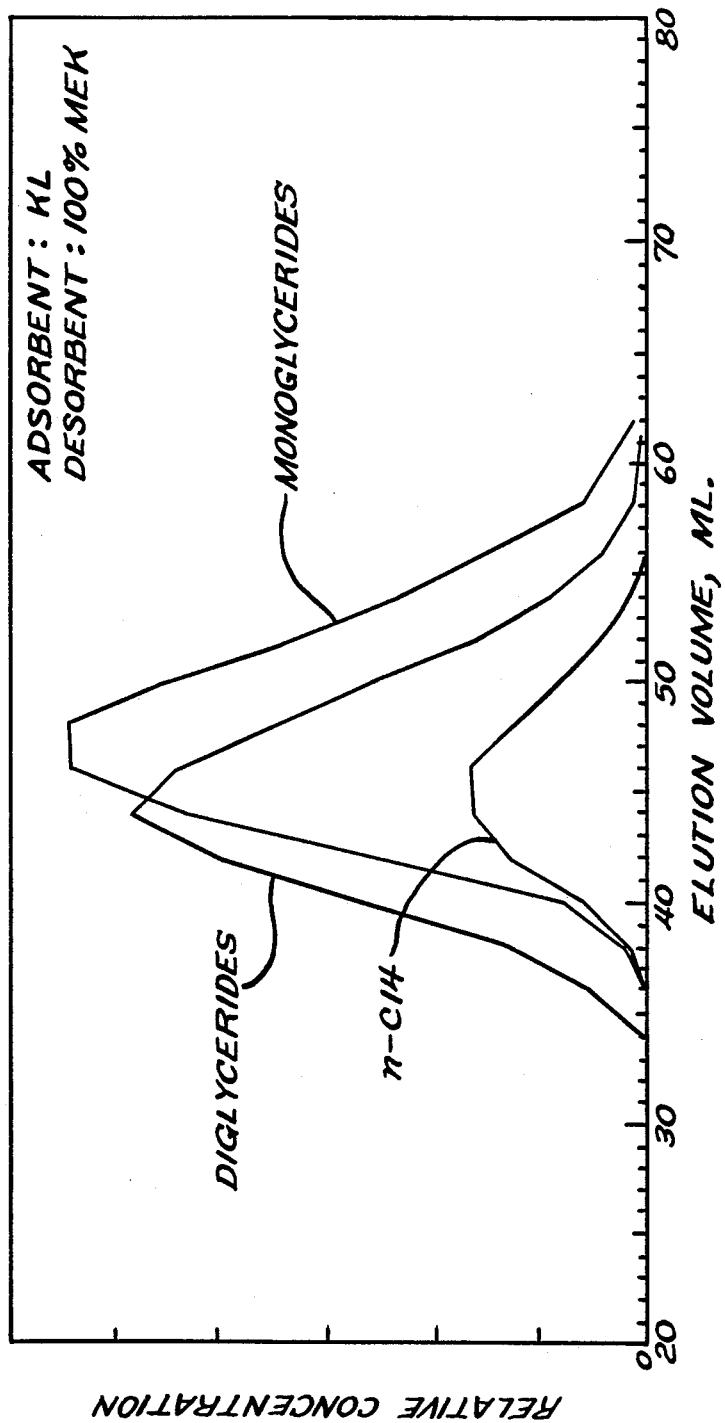

The experiment of Example I was repeated except that the adsorbent was a potassium-exchanged L type zeolite and the temperature was 120° C. The test is illustrated in FIG. 8, from which a retention volume for the monoglycerides of 2.4 cc was calculated, indicating that potassium-exchanged L zeolite exhibits good selectivity for monoglycerides over diglycerides.

EXAMPLE IX

Figure 9:
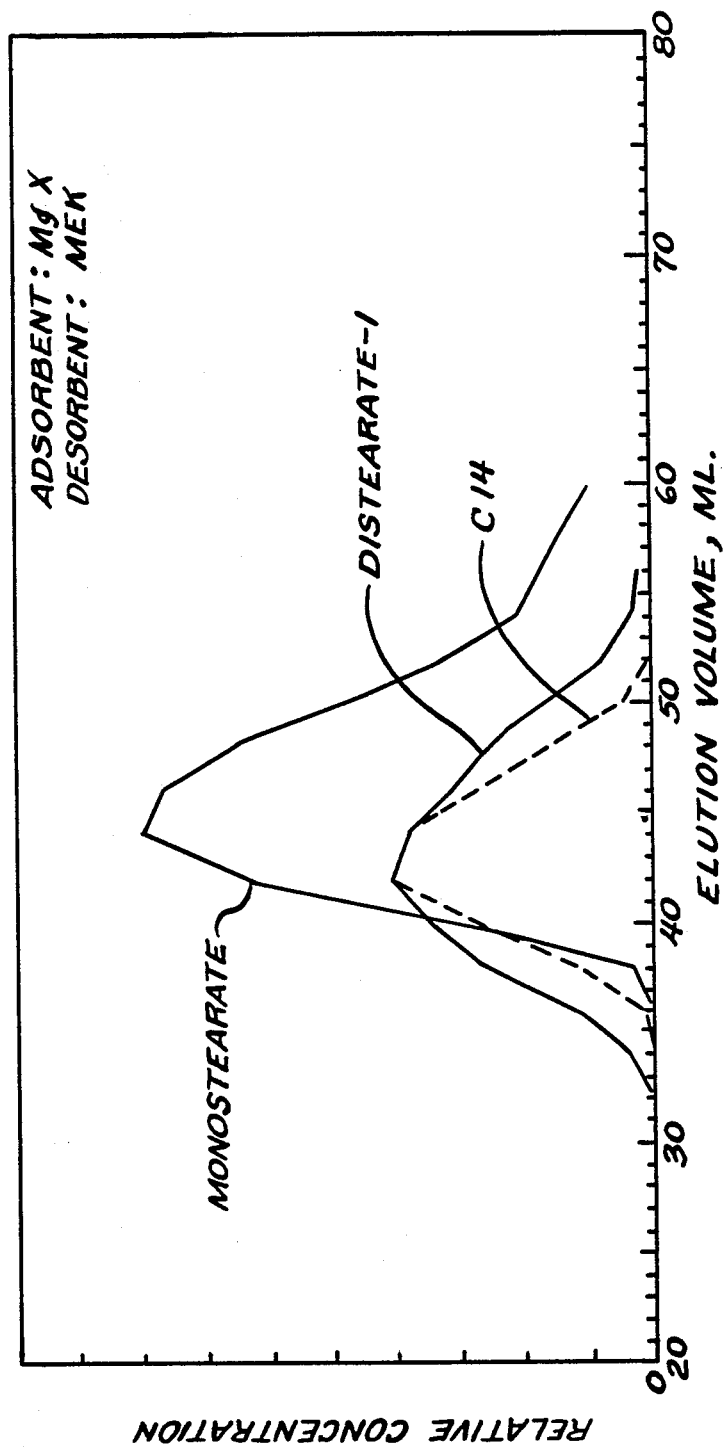

The experiment of Example VI was repeated except that the adsorbent was a magnesium-exchanged X zeolite. The test, shown in FIG. 9, indicates that the magnesium-exchanged X zeolite has adsorptive selectivity for monoglycerides, with a monoglyceride retention volume of 2.7 cc.

EXAMPLE X

This example illustrates the ability of our process, when operated in a preferred embodiment, which utilizes a continuous simulated moving bed countercurrent type of operation, and comprises a pilot plant scale testing apparatus known as a carousel unit described in detail in deRosset et al. U.S. Pat. No. 3,706,812, incorporated herein by reference. Briefly, the apparatus consists essentially of 24 serially connected adsorbent chambers having about 19.2 cc volume each. Total chamber volume of the apparatus is approximately 460 cc. The individual adsorbent chambers are serially connected to each other with relatively small diameter connecting piping and to a rotary type valve with other piping. The valve has inlet and outlet ports which direct the flow of feed and desorbent material to the chambers and extract and raffinate streams from the chambers. By manipulating the rotary valve and maintaining given pressure differentials and flow rates through the various lines passing into and out of the series of chambers, a simulated countercurrent flow is produced. The adsorbent remains stationary while fluid flows throughout the serially connected chambers in a manner which when viewed from any position within the adsorbent chambers is steady countercurrent flow. The moving of the rotary valve is done in a periodic shifting manner to allow a new operation to take place in the adsorbent beds located between the active inlet and outlet ports of the rotary valve. Attached to the rotary valve are input lines and output lines through which fluids to and from the process flow. The rotary valve contains a feed input line through which passes the feed mixture, and extract stream outlet line through which passes the desorbent material, i.e., methylethyl ketone, in admixture with iso-octane, monoglycerides and fatty acids, a desorbent material inlet line through which passes desorbent materials and a raffinate stream outlet line through which passes di- and triglycerides in admixture with desorbent material. Additionally, a flush material inlet line is used to admit flush material for the purpose of flushing feed components from lines which had previously contained feed material and which will subsequently contain the raffinate or extract stream. The flush material employed is iso-octane which then leaves the apparatus as part of the extract stream and raffinate stream. Additional apparatus details can be found in U.S. Pat. No. 3,706,812. In order to better understand the operations taking place within the apparatus reference can be made to D. B. Broughton, U.S. Pat. No. 2,985,589 and to D. B. Broughton et al., "The Separation of P-Xylene from C$_8$ Hydrocarbon Mixtures by the Parex Process," presented at the Third Joint Annual Meeting, American Institute of Chemical Engineers and Puerto Rican Institute of Chemical Engineers, San Juan, Puerto Rico, May 17 through May 20, 1970. These references describe in detail the basic operations taking place in the testing apparatus used in this embodiment, and although said references are concerned with the separation of hydrocarbons, the testing apparatus itself is perfectly suited for purposes of this embodiment.

The feed mixture to the apparatus was the glyceride mixture of Example I. The adsorbent used was a potassium-exchanged X faujasite, deactivated as in Example I. The desorbent was 25 volume % methylethyl ketone in iso-octane.

The operating parameters of the carousel unit were as follows:

1. A/F=2.6, where A is the selective pore volume of the adsorbent in cc and F is the feed rate tothe separation stage in cc/hr. The selective pore volume is that volume of the adsorbent which has the ability to selectively adsorb one component of a mixture over another.
2. Process temperature=70° C.
3. Valve cycle time=90 min.

A number of experiments, each of six hours duration, were conducted on the carousel unit. In these experiments it was observed that the free fatty acids were adsorbed along with the monoglycerides and so were separated with the extract, while the triglycerides were relatively unadsorbed like the diglycerides and so were separated with the raffinate.

Figure 10:
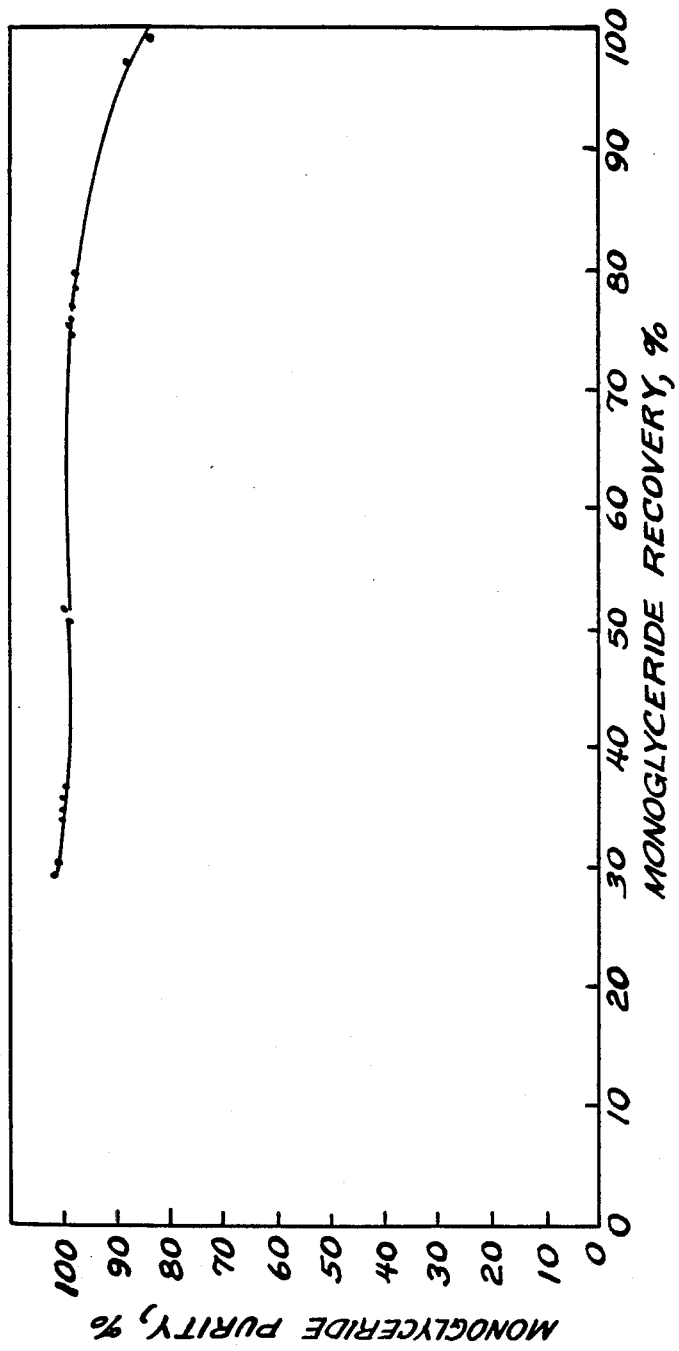

In these experiments the extract and raffinate streams were analyzed for their monoglyceride and fatty acid content, and di- and triglyceride content, respectively. The results of these experiments can be plotted as a curve of monoglyceride extract purity versus monoglyceride recovery and are illustrated in FIG. 10; the separation performance ranged from monoglyceride extract purity. of 88.1% at 97.5% recovery to 99+% purity at 51.3% recovery on a fatty acid free basis. It was further discovered that the monoglyceride extracts were easily freed of fatty acid content by cooling the extracts to 0° C., whereupon the monoglycerides precipitated and were filtered from the remaining mixture of desorbent and fatty acid. The raffinates, obtained under the conditions of high monoglyceride purity, were 97+% di- and triglycerides, with triglycerides constituting 10–12% of the raffinate glycerides.

Thus, it is clear from the above that the use of a KX adsorbent enables the separation of monoglycerides from a glyceride mixture containing mono-, di- and triglycerides and free fatty acids. Since the effects of different operating conditions on the product purity and yield have not been completely investigated, the results of the above tests are not intended to represent the optimums that might be achieved.

What is claimed is:

1. A continuous process separating monoglycerides from a mixture comprising monoglycerides and diglycerides said process comprising contacting said mixture at adsoprtion conditions with an adsorbent selected from the group consisting of an X type zeolite exchanged with Na, Mg, Li or K at exchangeable sites, a Y type zeolite exchanged with potassium or sodium at exchangeable sites, and an L type zeolite exchanged with potassium, thereby selectively adsorbing said monoglycerides thereon and desorbing said monoglycerides at desorption conditions and eluting said diglycerides with a desorbent selected from the group consisting of ketones having up to 7 carbon atoms and mixtures thereof with paraffin hydrocarbons.

2. The process of claim 1 wherein said desorbent is selected from the group consisting of methylethyl ketone, diethyl ketone, acetone and mixtures thereof with hexane.

3. The process of claim 1 wherein said desorbent material comprises methylethyl ketone.

4. The process of claim 1 wherein said adsorption conditions include a temperature within the range of from about 20° C. to about 200° C. and a pressure sufficient to maintain liquid phase.

5. A continuous process for separating a monoglyceride from a feed mixture comprising a monoglyceride and a diglyceride which process employs an adsorbent selected from the group consisting of an X zeolite exchanged with Na, Mg, Li or K or a Y zeolite exchanged with sodium or potassium or an L zeolite with potassium at exchangeable cationic sites which process comprises the steps of:
   (a) maintaining net fluid flow through a column of said adsorbent in a single direction, which column contains contains at least three zones having separate operational functions occurring therein and being serially interconnected with the terminal zones of said column connected to provide a continuous connection of said zones;
   (b) maintaining an adsorption zone in said column, said zone defined by the adsorbent located between a feed input stream at an upstream boundary of said zone and a raffinate output stream at a downstream boundary of said zone;
   (c) maintaining a purification zone immediately upstream from said adsorption zone, said purification zone defined by the adsorbent located between an extract output stream at an upstream boundary of said purification zone and said feed input stream at a downstream boundary of said purification zone;
   (d) maintaining a desorption zone immediately upstream from said purification zone, said desorption zone defined by the adsorbent located between a desorbent input stream at an upstream boundary of said zone and said extract output stream at a downstream boundary of said zone;
   (e) passing said feed mixture into said adsorption zone at adsorption conditions to effect the selective adsorption of said monoglyceride by said adsorbent in said adsorption zone and withdrawing a raffinate output stream from said adsorption zone;
   (f) passing a desorbent material comprising a ketone having up to 7 carbon atoms into said desorption zone at desorption conditions to effect the displacement of said monglyceride from the adsorbent in said desorption zone;
   (g) withdrawing an extract output stream comprising said monoglyceride and desorbent material from said desorption zone;
   (h) withdrawing a raffinate output stream comprising said diglyceride from said desorption zone; and
   (i) periodically advancing through said column of adsorbent in a downstream direction with respect to fluid flow in said adsorption zone, the feed input stream, raffinate output stream, desorbent input stream, and extract output stream to effect the shifting of zones through said adsorbent and the production of extract output and raffinate output stream.

6. The process of claim 5 wherein said desorbent material comprises methylethyl ketone, acetone, or diethyl ketone.

7. The process of claim 5 wherein said adsorption and desorption conditions include a temperature within the range of from about 20° C. to about 200° C. and a pressure sufficient to maintain liquid phase.

8. The process of claim 5 wherein a buffer zone is maintained immediately upstream from said desorption zone, said buffer zone is defined as the adsorbent located between the desorbent input stream as the downstream boundary of said buffer zone and the raffinate output stream at an upstream boundary of said buffer zone.

9. The process of claim 1 wherein said adsorbent is made substantially unreactive by reducing said adsorbent's basicity.

10. The process of claim 5 wherein the basicity of said adsorbent is reduced thereby substantially eliminating said adsorbent's reactivity.

* * * * *